United States Patent
Nevin

(10) Patent No.: US 9,005,530 B2
(45) Date of Patent: Apr. 14, 2015

(54) COMPRESSOR WITH AN INTERNAL DISINFECTING UV LIGHT SOURCE

(76) Inventor: Donald Nevin, Woodbury, NY (US)

( * ) Notice: Subject to any disclaimer, the term of this patent is extended or adjusted under 35 U.S.C. 154(b) by 568 days.

(21) Appl. No.: 12/833,112

(22) Filed: Jul. 9, 2010

(65) Prior Publication Data

US 2011/0005620 A1    Jan. 13, 2011

Related U.S. Application Data

(60) Provisional application No. 61/275,270, filed on Aug. 28, 2009, provisional application No. 61/274,209, filed on Aug. 14, 2009, provisional application No. 61/270,401, filed on Jul. 9, 2009, provisional application No. 61/336,880, filed on Jan. 28, 2010.

(51) Int. Cl.
*A61L 9/20* (2006.01)
*F04B 41/02* (2006.01)

(52) U.S. Cl.
CPC .. F04B 41/02 (2013.01); A61L 9/20 (2013.01)

(58) Field of Classification Search
CPC .......................... A61L 9/16–9/22; F04B 41/02
USPC .................. 422/4, 24, 121, 22; 137/565.18
See application file for complete search history.

(56) References Cited

U.S. PATENT DOCUMENTS

| | | | |
|---|---|---|---|
| 2,263,162 A | 11/1941 | Collins | |
| 3,768,970 A | 10/1973 | Malmin | |
| 3,966,407 A | 6/1976 | Zuckerberg et al. | |
| 4,448,750 A | 5/1984 | Fuesting | |
| 4,899,057 A | 2/1990 | Koji | |
| 5,185,532 A | 2/1993 | Zabsky et al. | |
| 5,527,704 A | 6/1996 | Wolf, Jr. et al. | |
| 5,616,172 A | 4/1997 | Tuckerman et al. | |
| 5,656,242 A | 8/1997 | Morrow et al. | |
| 6,497,840 B1 * | 12/2002 | Palestro et al. | 422/24 |
| 6,787,782 B1 | 9/2004 | Krosney et al. | |
| 6,797,044 B2 | 9/2004 | Ou Yang et al. | |
| 6,949,228 B2 | 9/2005 | Ou Yang et al. | |
| 7,094,378 B1 | 8/2006 | Goodrich, Jr. et al. | |
| 7,288,232 B2 | 10/2007 | Morrow et al. | |
| 2003/0190254 A1 * | 10/2003 | Falat | 422/4 |
| 2004/0047776 A1 | 3/2004 | Thomsen | |
| 2004/0213714 A1 | 10/2004 | Zhang | |

(Continued)

OTHER PUBLICATIONS

Mori, Hamamoto, Takahashi, Nakano, Wakikawa, Tachibana, Ikchara, Nakaya, Akutagawa, Kinouchi,—Development of a new water sterilization device with a 365 nm UV-LED, International Federation for Medical and Biological Engineering 2007, Tokushima, Japan.

*Primary Examiner* — Timothy Cleveland
(74) *Attorney, Agent, or Firm* — Epstein Drangel LLP; Robert L. Epstein

(57) ABSTRACT

The air compressor has an air intake, a tank, means for pressurizing the air in the tank and an air outlet connected to the tank. High power 365 nm UV LED light sources are mounted within the tank to disinfect the interior tank surface. The light source has a cover for protecting the light source which may take the form of a quartz diverging lens for directing the output of the light source toward the portion of the interior tank surface where fluid tends to accumulate, such as the bottom of the tank. Air flow is directed through the area proximate the light source to remove particles from the light source cover. The effect of this air flow can be amplified by creating turbulence proximate the light sources utilizing a member with an arcuate profile.

17 Claims, 3 Drawing Sheets

(56) References Cited

U.S. PATENT DOCUMENTS

| | | |
|---|---|---|
| 2004/0219056 A1 | 11/2004 | Tribelsky et al. |
| 2005/0017200 A1 | 1/2005 | Spector |
| 2005/0123436 A1 | 6/2005 | Cumberland |
| 2005/0163652 A1 | 7/2005 | Metzger et al. |
| 2005/0163668 A1 | 7/2005 | Crawford et al. |
| 2005/0220665 A1 | 10/2005 | Ding |
| 2005/0224335 A1 | 10/2005 | Carmignani et al. |
| 2005/0242013 A1 | 11/2005 | Hunter et al. |
| 2006/0005703 A1 | 1/2006 | Wang |
| 2006/0057020 A1 | 3/2006 | Tufo |
| 2006/0177356 A1 | 8/2006 | Miller |
| 2006/0207431 A1 | 9/2006 | Baca et al. |
| 2006/0275171 A1 | 12/2006 | Younts |
| 2006/0278075 A1 | 12/2006 | Blackner |
| 2006/0288865 A1 | 12/2006 | Lin |
| 2007/0101867 A1 | 5/2007 | Hunter et al. |
| 2007/0205382 A1 | 9/2007 | Gaska et al. |
| 2007/0253860 A1 | 11/2007 | Schroder |
| 2008/0131331 A1 | 6/2008 | Josserand et al. |
| 2008/0138241 A1 | 6/2008 | Naarup |
| 2008/0286146 A1 * | 11/2008 | Schroll et al. .......... 422/24 |

* cited by examiner

COMPRESSOR WITH AN INTERNAL DISINFECTING UV LIGHT SOURCE

CROSS-REFERENCE TO RELATED APPLICATIONS

Applicant claims priority on Provisional Patent Application No. 61/275,270 filed Aug. 28, 2009; Provisional Patent Application No. 61/274,209 filed Aug. 14, 2009; Provisional Patent Application No. 61/270,401 filed Jul. 9, 2009; and Provisional Patent Application No. 61/336,880 filed Jan. 28, 2010.

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to air compressors and more particularly to an air compressor with a source of UV light located within the tank which when energized disinfects the internal surfaces of the tank illuminated by the light source.

2. Description of Prior Art Including Information Disclosed Under 37 CFR 1.97 and 1.98

It is known that ultraviolet (UV) irradiation can effectively inactivate certain types of bacteria. Low pressure mercury lamps emitting ultraviolet light with a wavelength of 254 nm have been used for that purpose. However, mercury can be harmful and a lamp containing mercury can pose a hazard if subjected to shock or vibration. Accordingly, such lamps are not suitable for certain applications, including use in pressurized environments or where the lamp may be subject to vibrations.

It is also known that ultraviolet light-emitting diodes (LEDs) with an output wavelength of 365 nm can function as an effective sterilization device, see M. Mori et al., Medical Biological Engineering Computer Journal, (2007) 45: 1237-1241 entitled: "Development of a new water sterilization device with a 365 nm UV-LED".

In many dental and medical applications it is important to insure that the air supply to devices used to treat patients and in the presence of practitioners be as clean and germ free as possible. Air compressors are commonly used to supply air in such situations. To keep the air supply as clean as possible, various devices have been used to prevent air "backflow" from patients into the compressor. Further, various filtration and dehumidification methods have been employed to keep the air to the compressor as clean and dry as possible.

However, over time, bacteria and other organisms tend to form a film on the internal surface of the compressor tank. Those bacteria and organisms can contaminate the air being pumped from the compressor. Accordingly, there is a need to have a mechanism capable of continuously disinfecting the internal surfaces of the compressor tank without having to periodically dismantle or otherwise interrupt the operation of the compressor. Mercury lamps of the aforementioned type are not suitable for use in such an environment due to the pressure and vibration, the dangers associated with the use of a toxic substance and other factors.

Although numerous UV LEDs are currently commercially available, they are not effective as antibacterial devices because they are low power and emit in the 380 nm to 400 nm wavelength range. While, as mentioned above, mercury lamps that emit at the 254 nm wavelength can be very effective for sterilization and disinfection, it is not feasible to manufacture high power 254 nm LEDs at the present time.

Harnessing the 365 nm LEDs discussed by Mori et al. for use in disinfecting the internal surface of the compressor tank would be a significant improvement if certain technical difficulties associated with this environment are overcome. Ports can be created in the compressor tank wall to allow for the placement of one or more LEDs inside the tank. The LEDs can be oriented in a fashion which bathes the interior with germicidal UV light. The LEDs are strong enough to withstand the vibrations encountered in compressor operation.

The effectiveness of the LEDs can be maximized by directing the light from the LEDs to the areas of the tank where liquid tends to accumulate and hence where germs are most likely to grow. Spreading out the light beam from the LEDs to provide wider coverage can be achieved through the use of lenses. Mirrors and baffles may be used to direct the light as needed.

A protective cover made of quartz or similar situated between the LED and the air in the compressor tank can be used to protect the LED from the environment within the compressor tank. Preferably, the cover can take the form of a divergent lens which can shape the light beam as needed, thereby combining the protective and beam shaping qualities in a single component. Covers/lenses fabricated of other materials such as certain glasses and polymers may be used for this purpose, as well.

Over time, dust and other particles may settle on the LED or the cover/lens of the LED. This will reduce the effective output of the LED by absorbing some of the energy that would otherwise be available for germicidal effect. That energy is converted to heat and is re-emitted as IR radiation which is not useful in this situation.

This problem can be greatly reduced by utilizing a structure within the compressor tank which preferentially directs some of the incoming (or outgoing) airflow across the surface of the LED (or the cover/lens thereof) so as to continuously remove dust and other particles. This structure may take the form of stationary internal baffles, guides or vanes which create turbulence, vortexes or venturi in the area proximate the device. Alternately, a more complex structure such as an internal miniature turbine and fan blade may be employed. In the case of the latter, the turbine rotates due to a pressure differential between the air in the chamber and the moving incoming (or outgoing) air. These may be placed below pistons or other pressurizing mechanisms so that the temporary pressure differentials within the chamber cause air movement as described above. The motion of this air need not be continuous but may occur during part of the compression cycle or start up pressurization or, possibly, de-pressurization.

It is therefore a prime object of the present invention to provide a compressor with an internal disinfecting mechanism.

It is another object of the present invention to provide a compressor with an internal disinfecting mechanism in the form of UV light source.

It is another object of the present invention to provide a compressor with an internal disinfecting UV light source wherein the light source is a UV LED.

It is another object of the present invention to provide a compressor with an internal disinfecting UV light source wherein the light source is protected from the internal environment of the compressor by a cover or lens made of quartz, glass or polymer.

It is another object of the present invention to provide a compressor with an internal disinfecting UV light source wherein the beam from the light source is directed to portions of the internal surface of the compressor where liquid tends to pool.

It is another object of the present invention to provide a compressor with an internal disinfecting UV light source having means for removing dust or other particles from the path of light from the light source.

It is another object of the present invention to provide a compressor with an internal disinfecting LTV light source having means for removing dust or other particles from the path of light from the light source in the form of a structure for creating air turbulence proximate the surface of the light source.

BRIEF SUMMARY OF THE INVENTION

In general, the above objects are achieved by the present invention which relates to an air compressor having an air intake, a tank, means for pressurizing the air in the tank, an air outlet connected to the tank and means for disinfecting the interior surface of the tank, the disinfecting means including UV LED light source means mounted within the tank to illuminate the interior tank surface.

The light source means preferably includes a high power 365 nm UV LED light source. The light source preferably has a cover for protecting the light source. The cover may take the form of a lens for directing the output of the light source toward a portion of the interior tank surface. That portion of the interior tank surface preferably includes the portion of the interior tank surface where fluid tends to accumulate, such as the bottom of the tank.

Preferably, means are provided for preventing the accumulation of particles on the light source cover. The particle accumulation preventing means may take the form of means for directing air flow in the area proximate the light source to remove particles from the light source cover. The effect of this air flow can be amplified by creating turbulence proximate the light sources. The turbulence can be provided by a member with an arcuate profile along which the air flow is directed.

The light source means preferably includes a plurality of high power UV LED light sources. The light sources are preferably situated at spaced locations within said tank. The light sources are preferably situated in one or more rows parallel rows extending along the length of the tank at spaced locations around the circumference of the tank.

BRIEF DESCRIPTION OF THE SEVERAL VIEWS OF DRAWINGS

To these and to such other objects that may hereinafter appears, the present invention relates to a compressor with an internal disinfecting light source as described in detail in the following specification and recited in the annexed claims, taken together with the accompanying drawings, in which like numerals refer to like parts and in which:

DETAILED DESCRIPTION OF THE INVENTION

Figure 1:
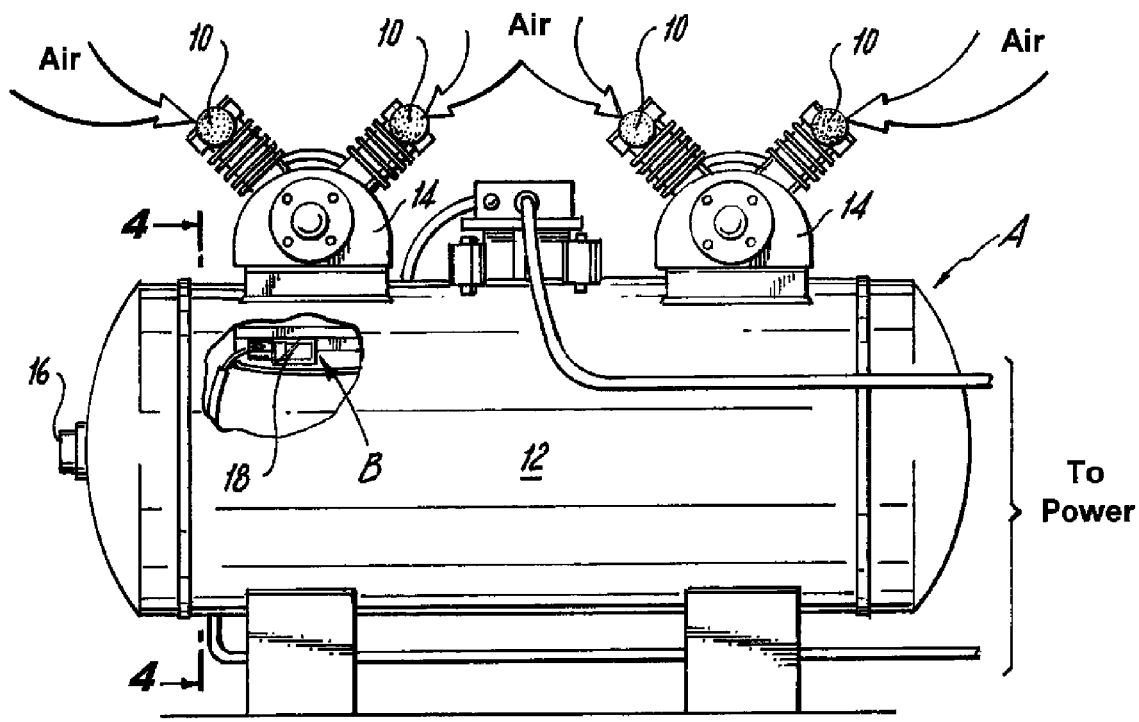
FIG. 1 is an elevation view of a compressor of the present invention.

As seen in FIG. 1, the present invention relates to an air compressor, generally designated A which can be used for any purpose that requires a source of pressurized air with reduced levels of harmful bacteria and other organisms, such as dental or medical apparatus of various types. Compressor A has multiple air intake ports 10, a tank 12 within which pressurized air from pressurizing pumps 14 accumulates, and an air outlet port 16 connected to tank 12 through which pressurized air in tank 12 exits the compressor.

Figure 2:
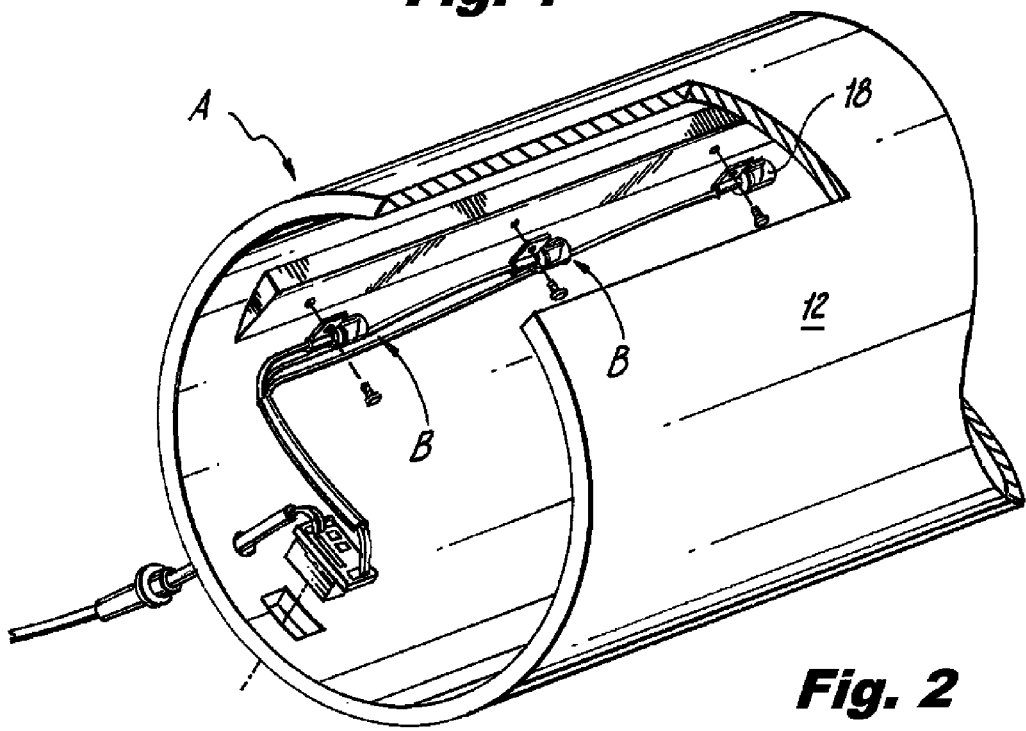
FIG. 2 is a partial cut away perspective view of a portion of the tank of the compressor of FIG. 1.

FIG. 1 includes a cut-away section of tank 12 so that one of the UV LED light source means, generally designated B, used for disinfecting the interior surface of the tank, is visible. One or more UV LED light source means B are mounted to the interior surface of the tank. As seen in FIG. 2, the light source means B may include several (three are shown) electrically connected light sources mounted at spaced locations along the length of the tank to provide illumination to large section of the interior tank surface.

Figure 3:
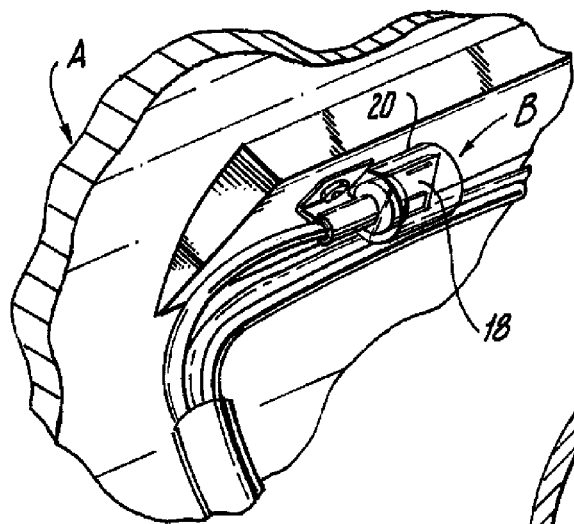
FIG. 3 is an enlarged perspective view of one of the UV LED light sources shown in FIG. 2.
Figure 4:
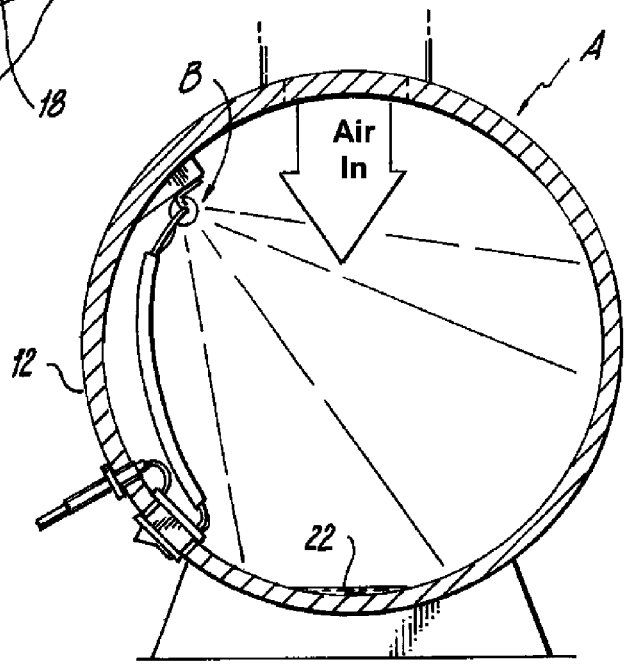
FIG. 4 is a cross-sectional side view taken along line 4-4 of FIG. 1 showing an embodiment with a plurality of light sources in a single line.
Figure 5:
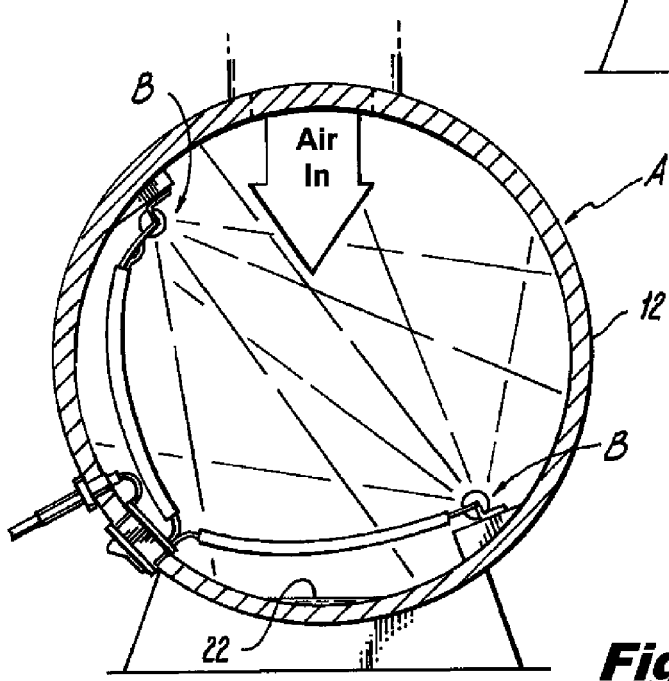
FIG. 5 is a view similar to FIG. 4 but showing an embodiment with two lines of light sources spaced within the tank.

As best seen in FIG. 3, each light source means B preferably includes a high power 365 nm UV LED light source 18. The light source 18 is situated within a cylindrical cover 20 which protects the light source from the environment within the tank. Cover 20 is preferably formed of quartz but other materials may be used, as well. Preferably, cover 20 includes a divergent lens for spreading the beam from the light source and directing the beam toward a portion of the interior tank surface. That portion of the interior tank surface preferably includes the portion of the interior tank surface where fluid 22 tends to accumulate, such as the bottom of the tank, as shown in FIGS. 4-7. As shown in FIG. 4, a single row of light sources B located near the top of the tank may be used to direct light to the bottom of the tank where liquid 22 tends to pool. As shown in FIG. 5, a second row of light sources located near the bottom of the tank may be used to direct light toward the interior surface at the top of the tank.

Preferably, means are provided for preventing the accumulation of particles on the light source cover. The particle accumulation preventing means may take the form of means for directing air flow in the area proximate the light source to remove particles from the light source cover. As seen in FIG. 4, the air flow can simply be directed passed the top set of light sources to keep the covers of those light sources particle free. As seen in FIG. 5, where there is a second set of light sources near the bottom of the tank, the downwardly directed air flow divides against the surface of the tank at the bottom and a portion of that air flow flows along the bottom of the tank and passed the second set of light sources to remove particles from the covers thereof.

Figure 6:
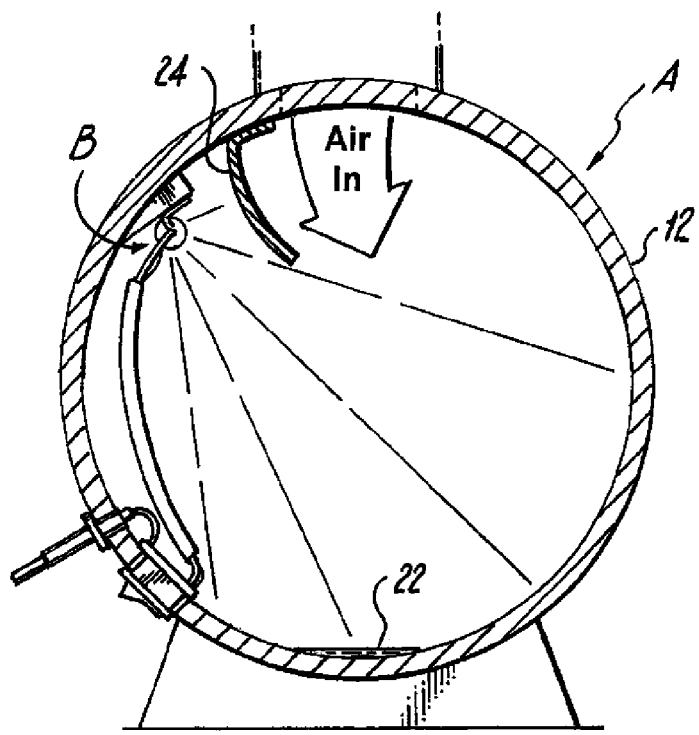
FIG. 6 is a cross-sectional side view of the compressor tank similar to that of FIG. 4 but including a member situated to direct the air flow to remove particles from the light source assembly.
Figure 7:
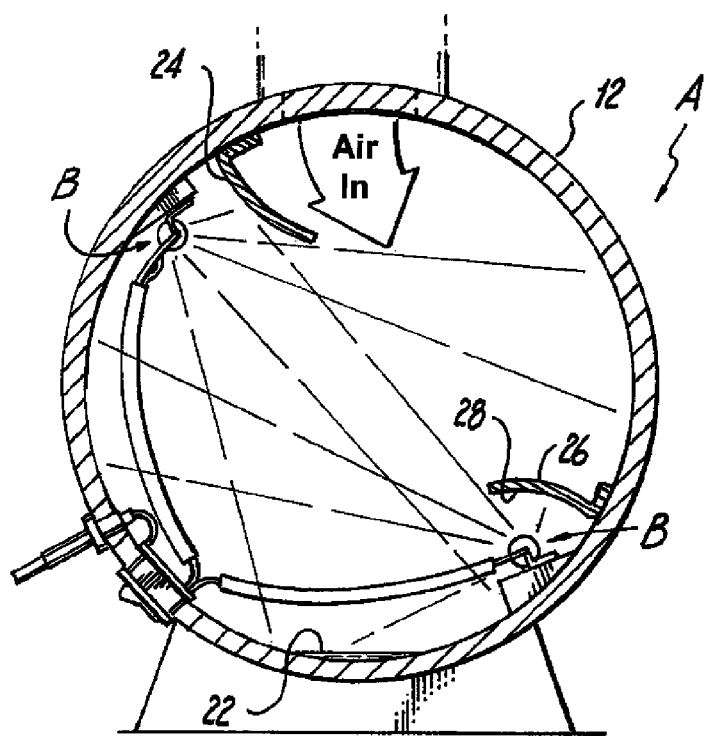
FIG. 7 is a cross-sectional side view of the compressor tank similar to that of FIG. 5 but including first and second members situated to direct the air flow to remove particles from the respective light source assemblies.

FIGS. 6 and 7 illustrate another preferred embodiment in which arcuate members are utilized to enhance the effectiveness of the air flow to remove particles from the light source covers by creating an area of turbulence proximate the covers. In FIG. 6, a single member 24 is situated between the location of the air input into the tank and the row of light sources near the top of the tank. Member 24 can take the form of a baffle, guide or vane which creates turbulence, vortexes or venture proximate the row of light sources near the top of the tank. As illustrated, member 24 has an arcuate profile to amplify this effect.

In FIG. 7, where a second row of light sources is present near the bottom of the tank, a second member 26 is situated adjacent the second row of light sources and creates turbulence, vortexes or ventures proximate the covers of the second row of light sources to remove the particles. Member 26, like member 24, has an arcuate profile to amplify the turbulent effect. Further, the concave surface 28 of member 26 is preferably silvered to create a mirror to reflect and focus a portion of the light from the light sources back to the area at the bottom of the tank where liquid 22 tends to pool.

It will now be appreciated that the present invention related to an air compressor having an air intake, a tank, means for pressurizing the air in the tank, an air outlet connected to the tank. Means are provided for disinfecting the interior surface of the tank. The disinfecting means including UV LED light source means mounted within the tank to illuminate the interior tank surface.

The light source means preferably includes a high power 365 nm UV LED light source. The light source preferably has a cover for protecting the light source formed of quartz or other suitable material. The cover preferably includes a lens for directing the output of the light source toward a portion of the interior tank surface. That portion of the interior tank surface preferably includes the portion of the interior tank surface where fluid tends to accumulate, such as the bottom of the tank.

While only a limited number of preferred embodiments of the present invention have been disclosed for purposes of illustration, it is obvious that many modifications and variations could be made thereto. It is intended to cover all of those modifications and variations which fall within the scope of the present invention, as defined by the following claims.

I claim:

1. An air compressor having a closed chamber for accumulating pressurized air, said chamber having an air inlet through which air may enter said chamber and an air outlet through which air may exit said chamber, said chamber being defined in part by a wall having an interior surface, a pressurizing pump located directly on said chamber and connected to said chamber air inlet for providing pressurizing air to said chamber and UV LED light source means mounted within said chamber, prior to said air outlet, for disinfecting said interior surface of said chamber wall.

2. The compressor of claim 1 wherein said light source means comprises a high power 365 nm UV LED.

3. The compressor of claim 1 wherein said light source means further comprises a UV LED and cover means for protecting said UV LED.

4. The compressor of claim 1 wherein said light source means comprises a UV LED and lens means for directing the light from said UV LED toward a portion of said interior surface.

5. The compressor of claim 1 wherein said interior surface of said chamber wall comprises a portion of said interior surface opposite to the portion of said interior wall where said UV LED light source means is mounted.

6. The compressor of claim 4 wherein said portion of said interior surface of said chamber wall comprises the bottom of said interior surface of said chamber wall.

7. The compressor of claim 1 comprising means for preventing particle buildup proximate said light source means.

8. The compressor of claim 1 further comprising means for directing air flow in the area proximate said light source means to prevent particle buildup on said light source means.

9. The compressor of claim 1 further comprising means for creating turbulence in the area proximate said light source means to prevent particle buildup on said light source means.

10. The compressor of claim 9 wherein said turbulence creating means comprises a member with an arcuate profile.

11. The compressor of claim 1 wherein said light source means comprises a plurality of high power UV LED light sources.

12. The compressor of claim 11 wherein said light sources are situated at spaced locations along said interior chamber wall.

13. The compressor of claim 11 wherein said light sources are situated in a row along said interior surface of said chamber wall.

14. The compressor of claim 1 wherein said light source means comprises a UV LED mounted to said interior surface of said chamber wall.

15. The compressor of claim 1 wherein said light source means comprises more than one UV LED mounted to said interior surface of said chamber wall.

16. An air compressor having a closed chamber for accumulating pressurized air, said chamber having an air inlet through which air may enter said chamber and an air outlet through which air may exit said chamber, said chamber being defined in part by a wall having an interior surface, a pressurizing pump connected directly to said chamber air inlet for providing pressurizing air to said chamber and UV LED light source means mounted within said chamber, prior to said air outlet, for disinfecting said interior surface of said chamber wall.

17. An air compressor having a closed chamber for accumulating pressurized air, said chamber having an air inlet through which air may enter said chamber and an air outlet through which air may exit said chamber, said chamber being defined in part by a wall having an interior surface, a pressurizing pump connected directly to said chamber for providing pressurizing air to said chamber air inlet and UV LED light source means mounted within said chamber, prior to said air outlet, for disinfecting said interior surface of said chamber wall.

* * * * *